US007756563B2

(12) United States Patent
Higgins et al.

(10) Patent No.: US 7,756,563 B2
(45) Date of Patent: Jul. 13, 2010

(54) GUIDANCE METHOD BASED ON 3D-2D POSE ESTIMATION AND 3D-CT REGISTRATION WITH APPLICATION TO LIVE BRONCHOSCOPY

(75) Inventors: William E. Higgins, State College, PA (US); Scott A. Merritt, State College, PA (US); Lav Rai, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 803 days.

(21) Appl. No.: 11/437,229

(22) Filed: May 19, 2006

(65) Prior Publication Data
US 2007/0015997 A1 Jan. 18, 2007

Related U.S. Application Data

(60) Provisional application No. 60/683,595, filed on May 23, 2005.

(51) Int. Cl.
*A61B 5/05* (2006.01)
(52) U.S. Cl. ...................... 600/407; 600/423
(58) Field of Classification Search .............. 600/407, 600/423
See application file for complete search history.

(56) References Cited

U.S. PATENT DOCUMENTS 4,791,934 A   12/1988   Brunnett (Continued)

FOREIGN PATENT DOCUMENTS

KR     20020041577    6/2002
WO     WO 2006076789  7/2006

OTHER PUBLICATIONS

Lee et al., Pose Estimation Via Gauss-Newton-on-manifold, 16th International Symposium Mathematical theory of Network and System (MTNS), Leuven, 2004.*

(Continued)

*Primary Examiner*—Long V Le
*Assistant Examiner*—Saurel J Selkin
(74) *Attorney, Agent, or Firm*—Gifford, Krass, Sprinkle, Anderson & Citkowski, P.C.

(57) ABSTRACT

A method provides guidance to the physician during a live bronchoscopy or other endoscopic procedures. The 3D motion of the bronchoscope is estimated using a fast coarse tracking step followed by a fine registration step. The tracking is based on finding a set of corresponding feature points across a plurality of consecutive bronchoscopic video frames, then estimating for the new pose of the bronchoscope. In the preferred embodiment the pose estimation is based on linearization of the rotation matrix. By giving a set of corresponding points across the current bronchoscopic video image, and the CT-based virtual image as an input, the same method can also be used for manual registration. The fine registration step is preferably a gradient-based Gauss-Newton method that maximizes the correlation between the bronchoscopic video image and the CT-based virtual image. The continuous guidance is provided by estimating the 3D motion of the bronchoscope in a loop. Since depth-map information is available, tracking can be done by solving a 3D-2D pose estimation problem. A 3D-2D pose estimation problem is more constrained than a 2D-2D pose estimation problem and does not suffer from the limitations associated with computing an essential matrix. The use of correlation-based cost, instead of mutual information as a registration cost, makes it simpler to use gradient-based methods for registration.

29 Claims, 6 Drawing Sheets

U.S. PATENT DOCUMENTS

| | | | |
|---|---|---|---|
| 5,740,802 | A | 4/1998 | Nafis et al. |
| 5,748,767 | A | 5/1998 | Raab |
| 5,765,561 | A | 6/1998 | Chen et al. |
| 5,769,640 | A * | 6/1998 | Jacobus et al. ............. 434/262 |
| 5,776,050 | A | 7/1998 | Chen et al. |
| 5,782,762 | A | 7/1998 | Vining |
| 5,792,147 | A | 8/1998 | Evans et al. |
| 5,830,145 | A | 11/1998 | Tenhoff |
| 5,891,034 | A | 4/1999 | Bucholz |
| 5,901,199 | A | 5/1999 | Murphy et al. |
| 5,920,319 | A | 7/1999 | Vining et al. |
| 5,963,612 | A | 10/1999 | Navab |
| 5,963,613 | A | 10/1999 | Navab |
| 5,971,767 | A | 10/1999 | Kaufman et al. |
| 5,999,840 | A | 12/1999 | Grimson et al. |
| 6,006,126 | A | 12/1999 | Cosman |
| 6,016,439 | A | 1/2000 | Acker |
| 6,049,582 | A | 4/2000 | Navab |
| 6,078,701 | A * | 6/2000 | Hsu et al. ................ 382/294 |
| 6,083,162 | A | 7/2000 | Vining |
| 6,190,395 | B1 | 2/2001 | Williams |
| 6,201,543 | B1 | 3/2001 | O'Donnell et al. |
| 6,236,743 | B1 | 5/2001 | Pratt |
| 6,241,657 | B1 | 6/2001 | Chen et al. |
| 6,272,366 | B1 | 8/2001 | Vining |
| 6,311,116 | B1 | 10/2001 | Lee et al. |
| 6,334,847 | B1 | 1/2002 | Fenster et al. |
| 6,343,936 | B1 | 2/2002 | Kaufman et al. |
| 6,351,573 | B1 | 2/2002 | Schneider |
| 6,366,800 | B1 | 4/2002 | Vining et al. |
| 6,442,417 | B1 | 8/2002 | Shahidi et al. |
| 6,470,207 | B1 | 10/2002 | Simon et al. |
| 6,491,702 | B2 | 12/2002 | Heilbrun et al. |
| 6,514,082 | B2 | 2/2003 | Kaufman et al. |
| 6,535,756 | B1 | 3/2003 | Simon et al. |
| 6,546,279 | B1 | 4/2003 | Bova et al. |
| 6,593,884 | B1 | 7/2003 | Gilboa et al. |
| 6,674,879 | B1 | 1/2004 | Weisman et al. |
| 6,675,032 | B2 | 1/2004 | Chen et al. |
| 6,690,960 | B2 * | 2/2004 | Chen et al. ................ 600/407 |
| 6,694,163 | B1 | 2/2004 | Vining |
| 6,771,262 | B2 | 8/2004 | Krishnan |
| 6,785,410 | B2 | 8/2004 | Vining et al. |
| 6,816,607 | B2 | 11/2004 | O'Donnell et al. |
| 6,819,785 | B1 | 11/2004 | Vining et al. |
| 6,859,203 | B2 | 2/2005 | van Muiswinkel et al. |
| 6,909,913 | B2 | 6/2005 | Vining |
| 6,920,347 | B2 | 7/2005 | Simon et al. |
| 6,928,314 | B1 | 8/2005 | Johnson et al. |
| 6,947,584 | B1 | 9/2005 | Avila et al. |
| 6,980,682 | B1 | 12/2005 | Avinash et al. |
| 7,019,745 | B2 | 3/2006 | Goto et al. |
| 7,343,036 | B2 | 3/2008 | Kleen et al. |
| 2001/0035871 | A1 * | 11/2001 | Bieger et al. ............... 345/630 |
| 2003/0152897 | A1 | 8/2003 | Geiger |
| 2003/0216631 | A1 * | 11/2003 | Bloch et al. ................ 600/407 |
| 2004/0209234 | A1 | 10/2004 | Geiger |
| 2004/0252870 | A1 | 12/2004 | Reeves et al. |
| 2005/0078858 | A1 | 4/2005 | Yao et al. |
| 2005/0084833 | A1 * | 4/2005 | Lacey et al. ................ 434/262 |
| 2005/0096526 | A1 | 5/2005 | Reinschke |
| 2005/0272999 | A1 | 12/2005 | Guendel |
| 2006/0084860 | A1 | 4/2006 | Geiger et al. |
| 2008/0262297 | A1 | 10/2008 | Gilboa et al. |

OTHER PUBLICATIONS

Deligianni, F., A. Chung, and G. Yang. "Patient-specific bronchoscope simulation with pq—space-based 2D/3D registration." Computer Aided Surgery, vol. 9, No. 5, p. 215-226 (2004).

Lee, P.Y. and J.B. Moore. "Pose Estimation via Gauss-Newton-on-manifold." 16th International Symposium on Mathematical Theory of Network and System (MTNS), Leuven, 2004.

Hamadeh, A., S. Lavallee, and P. Cinquin. "Automated 3-Dimensional Computed Tomographic and Fluoroscopic Image Registration." Computer Aided Surgery 1998, vol. 3: p. 11-19.

Roberson, R.E. and P.W. Likins. "A Linearization Tool for Use with Matrix Formalisms of Rotational Dynamics." Archive of Applied Mathematics, vol. 37, No. 6: p. 388-392. Nov. 1969.

Asano, F., Y. Matsuno, T. Matsushita, H. Kondo, Yoshio Saito, A. Seko, and Y. Ishihara. "Transbronchial Diagnosis of a Pulmonary Peripheral Small Lesion Using an Ultrathin Bronchoscope with Virtual Bronchoscopic Navigation." Journal of Bronchology (2002), vol. 9, No. 2, p. 108-111.

Geiger, B., G.M. Weiner, K. Schulze, J. Bilger, P. Krebs, K. Wolf, T.Albrecht. "Virtual Bronchoscopy Guidance System for Transbronchial Needle Aspiration." Proceedings of SPIE vol. 5746 (2005).

Grimson, W.E.L., G.J. Ettinger, S.J. White, T. Lozano-Perez, W.M. Wells III, and R. Kikinis. "An Automatic Registration Method for Frameless Stereotaxy, Image Guided Surgery, and Enhanced Reality Visualization." IEEE Transactions on Medical Imaging, Apr. 1996, vol. 15, No. 2, p. 129-140.

Helferty, J.P., A.J. Sherbondy, A.P. Kiraly, and W.E. Higgins. "Computer-based System for the Virtual Endoscopic Guidance of Bronchoscopy." (believed to have been offered for sale, publicly used, and/or published prior to the filing date of this application).

Hopper, K.D., T.A. Lucas, K. Gleeson, J.L. Stauffer, R. Bascom, D. T. Mauger, R. Mahraj. "Transbronchial Biopsy with Virtual CT Bronchoscopy and Nodal Highlighting." Radiology Nov. 2001, vol. 221, No. 2, p. 531-536.

Maurer, C.R., J.M. Fitzpatrick, M.Y. Wang, R.L. Galloway, Jr., R.J. Maciunas, and G.S. Allen. "Registration of Head Volume Images Using Implantable Fiducial Markers." IEEE Transactions on Medical Imaging, Aug. 1997, vol. 16, No. 4, p. 447-462.

McAdams, H.P., P.C. Goodman, and P. Kussin. "Virtual Bronchoscopy for Directing Transbronchial Needle Aspiration of Hilar and Mediastinal Lymph Nodes: A Pilot Study." AJR May 1998, vol. 170, p. 1361-1364.

Merritt, S.A., L. Rai, and W.E. Higgins. "Real-Time CT-Video Registration for Continuous Endoscopic Guidance." (believed to have been offered for sale, publicly used, and/or published prior to the filing date of this application).

Mori, K., T. Enjoji, D. Deguchi, T. Kitasaka, Y. Suenaga, J. Toriwaki, H. Takabatake, and H. Natori. "New image similarity measures for bronchoscope tracking based on image registration between virtual and real bronchoscopic images." (believed to have been offered for sale, publicly used, and/or published prior to the filing date of this application).

Rai, L., S.A. Merritt, and W.E. Higgins. "Real-time Image-based Guidance Method for Lung-Cancer Assessment." (believed to have been offered for sale, publicly used, and/or published prior to the filing date of this application).

Sato, Y., M. Nakamoto, Y. Tamaki, T. Sasama, I. Sakita, Y. Nakajima, M. Monden, and S. Tamura. "Image Guidance of Breast Cancer Surgery Using 3-D Ultrasound Images and Augmented Reality Visualization." IEEE Transactions on Medical Imaging, Oct. 1998, vol. 17, No. 5, p. 681-693.

Schwarz, Y., A.C. Mehta, A. Ernst, F. Herth, A. Engel, D. Besser, and H. D. Becker. "Electromagnetic Navigation during Flexible Bronchoscopy." Respiration 2003, vol. 70, p. 516-522.

Shinagawa, N., K. Yamazaki, Y. Onodera, K. Miyasaka, E. Kikuchi, H. Dosaka-Akita, and M. Nishimura. "CT-Guided Transbronchial Biopsy Using an Ultrathin Bronchoscope with Virtual Bronchoscopic Navigation." Chest, Mar. 2004, vol. 25, p. 1138-1143.

Shoji, H., K. Mori, J. Sugiyama, Y. Suenaga, J. Toriwaki, H. Takabatake, and H. Natori. "Camera motion tracking of real endoscope by using virtual endoscopy system and texture information." Proceedings of SPIE vol. 4321, p. 122-133 (2001).

Stefansic, J.D., A.J. Herline, Y. Shyr, W.C. Chapman, J.M. Fitzpatrick, B.M. Dawant, and R.L. Galloway, Jr. "Registration of Physical Space to Laparoscopic Image Space for Use in Minimally Invasive Hepatic Surgery." IEEE Transactions on Medical Imaging, Oct. 2000, vol. 19, No. 10, p. 1012-1023.

Turcza, P. and M. Duplaga. "Navigation Systems Based on Registration of Endoscopic and CT-derived Virtual Images for Bronchofiberoscopic Procedures." Studies in Health Technology and Informatics, vol. 105, p. 253-263 (2004).

White, C.S., E.A. Weiner, P. Patel, and E.J. Britt. "Transbronchial Needle Aspiration: Guidance with CT Fluoroscopy." Chest 2000, vol. 118, No. 6, p. 1630-1638.

Higgins, W., W.J.T. Spyra, R.A. Karwoski, and E.L. Ritman. "System for Analyzing High-Resolution Three-Dimensional Coronary Angiograms." IEEE Transactions on Medical Imaging, Jun. 1996, vol. 15, No. 3, p. 377-385.

Brady, M.L., W.E. Higgins, K. Ramaswamy. "Interactive navigation inside 3D radiological images." IEEE 1995, p. 33-40.

Higgins, W.E. and K. Ramaswamy. "Toward dynamic visualization for endoscopy simulation." IEEE 1994, p. 700-701.

Bricault, I., G. Ferretti, and P. Cinquin. "Registration of Real and CT-Derived Virtual Bronchoscopic Images to Assist Transbronchial Biopsy." IEEE Transactions on Medical Imaging, Oct. 1998, vol. 17, No. 5, p. 703-714.

Sherbondy, A.J., A.P. Kiraly, A.L. Austin, J.P. Helferty, S. Wan, J.Z. Turlington, T. Yang, C. Zhang, E.A. Hoffman, and G. McLennan. "Virtual Bronchoscopic approach for combining 3D CT and Endoscopic Video." Proceedings of SPIE 2000, vol. 3978, No. 104.

Helferty, J.P., A.J. Sherbondy, A.P. Kiraly, J.Z. Turlington, E.A. Hoffman, G. McLennan, W.E. Higgins. "Experiments in virtual-endoscopic guidance of bronchoscopy." Proceedings of SPIE 2001, vol. 4321, No. 111.

Helferty, J.P. and W.E. Higgins. "Combined endscopic video tracking and virtual 3D CT registration for surgical guidance." Proceedings of the 2002 International Conference on Image Processing, vol. 2, pp. 961-964.

Higgins, W.E., J.P. Helferty, and D.R. Padfield. "Integrated bronchoscopic video tracking and 3D CT registration for virtual bronchoscopy." Proceedings of SPIE 2003, vol. 5031, No. 80.

Kiraly, A.P., J.P. Helferty, E.A. Hoffman, G. McLennan, W.E. Higgins. "Three-dimensional path planning for virtual bronchoscopy." IEEE Transactions on Medical Imaging 2004, vol. 23, No. 11, pp. 1365-1379.

Helferty, J.P., E.A. Hoffman, G. McLennan, W.E. Higgins. "CT-video registration accuracy for virtual guidance of bronchoscopy." Proceedings of SPIE 2004, vol. 5369, pp. 150-164.

Higgins, W.E., L. Rai, S.A. Merritt, K. Lu, N. T. Linger, and K.C. Yu. "3D image fusion and guidance for computer-assisted bronchoscopy." Proceedings of SPIE 2005, vol. 6016.

Asano, F., Y Matsuno, N. Shinagawa, K. Yamazaki, T. Suzuki, T. Ishida, and H. Moriya. "A Virtual Bronchoscopic Navigation System for Pulmonary Peripheral Lesions." Chest 2006, vol. 130, No. 2, pp. 559-566.

Kukuk, M. "Modeling the Internal and External Constraints of a Flexible Endoscope for Calculating its Workspace: Application in Transbronchial Needle Aspiration Guidance." Proceedings of SPIE 2002, vol. 4681, pp. 539-550.

Gibbs, J.D. and W.E. Higgins. "3D Path Planning and Extension for Endoscopic Guidance." Proceedings of SPIE 2007, vol. 6509.

Mori, K., S. Ema, T. Kitasaka, Y. Mekada, I. Ide, H. Murase, Y. Suenaga, H. Takabatake, M. Mori, and H. Natori. "Automated Nomenclature of Bronchial Branches Extracted from CT Images and Its Application to Biopsy Path Planning in Virtual Bronchoscopy." Medical Image Computing and Computer-Assisted Intervention 2005, Lecture Notes in Computer Science 3750, pp. 854-861.

Kiraly, et al., 3D human airway segmentation for virtual bronchoscopy, *Proceedings of SPIE*, 4683: 16-29, 2002.

Lucas, et al., An iterative image registration technique with an application to stereo vision, *Proceedings of the 7th International Joint Conference on Artificial Intelligence (IJCAI '81)*, Apr., 1981, pp. 674-679.

Minami, et al., Interbronchoscopist variability in the diagnosis of lung cancer by flexible bronchoscopy, *Chest*, 105:1658-1662, 1994.

Okatani, et al., Shape reconstruction from an endoscope image by shape from shading technique for a point light source at the projection center, *Computer Vision and Image Understanding*, 66:119-131, 1997.

Shum, et al., Systems and experiment paper: construction of panoramic image mosaics with global and local alignment, *International Journal of Computer Vision*, 36(2): 101-130, 2000.

Shum, et al, Panoramic image mosaics, Microsoft Research, Technical Report MSR-TR-97- 23, 1997.

Swift, et al., Automatic axis generation for virtual bronchoscopic assessment of major airway obstructions, Computerized Medical Imaging and Graphics, 26: 103-118, 2002.

Asano, et al., Transbronchial diagnosis of a pulmonary peripheral small lesion using an ultrthin bronchoschope with virtual bronchoscopic navigation, Journal of Bronchology, 9: 108-11, 2002.

Helferty, et al., Technique for registering 3D virtual CT images to endoscopic video, IEEE Image Processing, 893-896, 2001.

Baker, et al., Equivalence and efficiency of image alignment algorithms, Proceedings of the 2001 Conference on Computer Vision and Pattern Recognition, 1090-1097.

Bricault, et al., Registration of real and CT-derived virtual bronchoscopic images to assist transbronchial biopsy, IEEE Transactions of Medical Imaging, 17(5):703-714, 1998.

Deguchi, et al., Camera motion tracking of real bronchoscope using epipolar geometry analysis and CT derived bronchoscopic images, Proceedings of SPIE, 4683: 30-41, 2002.

Heralick, et al., Analysis and solutions of the three point perspective pose estimation problem, Proceedings Computer vision and pattern recognition, IEEE Computer Society Conference, 592-598, 1991.

Harris, et al., A combined corner and edge detector, Proceedings of the Fourth Alvey Vision Conference, 147-151, 1988.

Horaud, et al., A analytic solution for the perspective 4-point problem, Computer Vision, Graphics, and Image Processing, 47:33-44, 1989.

Fischler, et al., Random sample consensus: a paradigm for model fitting with application to image analysis and automated cartography, Communications of the ACM, 24(6): 381-395, 1981.

Zuliani, et al., A mathematical comparison of point detectors, Proceedings of the 2004 IEEE Computer Society Conference on Computer Vision and Pattern Recognition Workshops.

Ansar, et al., Linear pose estimation from points or lines, IEEE Transactions on Pattern Analysis and Machine Intelligence, 25(5):578:589, 2003.

Mori, et al., A method for tracking the camera motion of real endoscope by epipolar geometry analysis and virtual endoscopy system, Lecture Notes in Computer Science, 2208: 1-8, 2001.

Shi, et al., Good features to track, IEEE Conference on Computer Vision and Pattern Recognition, 593-600, 1994.

Triggs, B., Detecting keypoints with stable position, orientation, and scale under illumination changes, Lecture Notes on Computer Science, 3024: 100-113, 2004.

Quan, et al., Linear N-point camera pose determination, IEEE Transactions on Pattern Analysis and Machine Intelligence, 21(8): 774-780, 1999.

Heralick, et al., Pose estimation from corresponding point data, IEEE Transaction on Systems, Man, and Cybernetics, 19(6): 1426-1446, 1989.

Lowe, D., Fitting parameterized three-dimensional models to images, IEEE Transaction on Pattern Analysis and Machine Intelligence, 13(5):441-450, 1991.

Hager, et al., Fast and globally convergent pose estimation from video images, IEEE Transactions on Pattern Analysis and Machine Intelligence, 22(6):610-622, 2000.

Hartley, et al., Multiple View Geometry in Computer Vision, Cambridge University Press, ISBN:0521623049, pp. 238, 239, 281, 2000.

Higgins, et al., Integrated bronchoscopic video tracking and 3D CT registration for virtual bronchoscopy, Medical Imaging 2003: Physiology and Function: Methods, Systems, and Applications.

Mori, et al., New image similarity measures for bronchoscope tracking based on image registration between virtual and real bronchoscopic images, Medical Imaging 2004: Physiology, Function, and Structure from Medical Images, 165-176.

Shoji, et al., Camera motion tracking of real endoscope by using virtual endoscopy system and texture information, Medical Imaging 2001: Physiology and function from Multidimensional Images.

Helforty, et al., Combined endoscopic video tracking and virtual 3D CT registration for surgical guidance, IEEE International Conference on Image Processing, 2002.

Helferty, J., Image-guided endoscopy and its application to pulmonary medicine, A Thesis in Electrical Engineering, The Penns Ivania State University, 2002.

* cited by examiner

Figure 3. Method.

GUIDANCE METHOD BASED ON 3D-2D POSE ESTIMATION AND 3D-CT REGISTRATION WITH APPLICATION TO LIVE BRONCHOSCOPY

REFERENCE TO RELATED APPLICATION

This application claims priority to U.S. Provisional Patent Application Ser. No. 60/683,595, filed May 23, 2005, the entire content of which is incorporated herein by reference.

GOVERNMENT SPONSORSHIP

This invention was made with government support under Grant No. R01 CA074325, awarded by the National Institutes of Health. The Government has certain rights in the invention.

FIELD OF THE INVENTION

This invention relates generally to bronchoscopy and, in particular, to a method that provides guidance to the physician during a live bronchoscopy or other applications.

BACKGROUND OF THE INVENTION

For lung cancer assessment, the physician needs to perform a biopsy of the suspect cancer sites, such as the peripheral nodules or mediastinal lymph nodes. Such sites are first identified by analyzing the 3D CT image data of the chest. Later, during bronchoscopy, the physician attempts to reach these sites with the help of the live video obtained from a bronchoscope. The success of a standard bronchoscopy depends heavily on the skill level and experience of the physician. The success of the bronchoscopy could be increased if the physician received some form of guidance during the procedure.

Several guidance methods have been suggested in the past few years [1-5]. All of them use a CT-based (virtual) endoluminal rendering of the airway surface to obtain both the depth and visual data. They try to find the 3D location and orientation of the bronchoscope (pose) using the virtual renderings and incoming video frames. Bricault et al. proposed a method to register the bronchoscopic video (real) and 3D CT virtual bronchoscopic images [1]. The method uses the segmentation and shape from shading techniques to find the 3D surface for the real image and then does a 3D-3D registration of the computed surface with the virtual surface.

Mori et al. proposed a method which first tracks a set of points across the real frames to estimate the bronchoscopic motion by computing the essential matrix and then does an estimation of the residual motion using image registration by Powell's method [3]. In [5], Mori et al. use a Kalman filter to predict bronchoscope motion and a new similarity measure to reduce the image area to be registered. Helferty et al. use a coarse tracking and fine registration approach [2,6]. The tracking is implemented by using the standard optical-flow constraint equation and depth-map information from the virtual rendering to estimate the motion parameters. The registration is done by maximizing the mutual information between the real and virtual image using the simplex method.

The method proposed by Bricault et al. does not involve tracking and is limited to the bifurcation images [1]. The method of Mori et al. computes the essential matrix for tracking [3] and Powell's method for registration. The approach has three limitations. Firstly, the use of Powell's method makes the registration step slow. Secondly, the essential matrix cannot be determined if a subset of points are coplanar [7]. Thirdly, a translation can only be recovered up to a scale from the estimated essential matrix [7]. The optical-flow approach taken by Helferty et al. for tracking is slow since it involves iterative warping and computation of gradients for the images [2, 6]. Use of simplex method makes the registration step slow as well.

SUMMARY OF THE INVENTION

This invention broadly resides in a system and method for providing guidance in conjunction with a diagnostic procedure. The method includes the steps of providing previously acquired image data of a body lumen, acquiring live image data of the body lumen, and registering the previously acquired image data and the live image data in real time or near real-time. In the preferred embodiment, the registration is used to guide an instrument such as an endoscope, bronchoscope, colonoscope or laparoscope.

The previously acquired image data may be derived from virtual image data, including computerized tomographic (CT) slices. Alternatively, the previously acquired image data may be derived from a prerecorded video image. The live image data may be derived from video data acquired during the diagnostic procedure or from a stream of incoming virtual images.

The invention has particular applicability to guidance during a live bronchoscopy. The 3D motion of the bronchoscope is estimated using a fast coarse tracking step followed by a fine registration step as necessary for correction purposes. The tracking is based on finding a set of corresponding feature points across a plurality of consecutive bronchoscopic video frames, then estimating for the new pose of the bronchoscope.

In the preferred embodiment the pose estimation is based on linearization of the rotation matrix. By giving a set of corresponding points across the current bronchoscopic video image, and the CT-based virtual image as an input, the same method can also be used for manual registration.

The fine registration step is a gradient-based Gauss-Newton method that maximizes the correlation-based cost between the bronchoscopic video image and the CT-based virtual image. The continuous guidance is provided by estimating the 3D motion of the bronchoscope in a loop.

Since depth-map information is available, the tracking can be done by solving a 3D-2D pose estimation problem. A 3D-2D pose estimation problem is more constrained than a 2D-2D pose estimation problem and does not suffer from the limitations associated with computing an essential matrix. The use of correlation-based cost, instead of mutual information as a registration cost, makes it simpler to use gradient-based methods for registration.

BRIEF DESCRIPTION OF THE DRAWINGS

FIGS. 4A-4C demonstrate the manual registration step applied to a pair of virtual images, wherein

FIG. 6A-6C show the result of using the method by Lu et al. for pose estimation, wherein

DETAILED DESCRIPTION OF THE INVENTION

As discussed in the Summary of the Invention, to track the 3D motion of the bronchoscope, we use the fast coarse tracking and subsequent fine registration approach. We propose a 3D-2D pose estimation algorithm for tracking and a gradient-based Gauss-Newton method for registration which uses correlation-based cost as its cost function.

It should be noted that even if the tracking algorithm is 100 percent accurate, one cannot avoid the fine registration step. This is because the 3D virtual surface data is not an accurate representation of the actual airway tree. The presence of the imaging artifacts, segmentation errors and issues related to lung capacity cause this. Hence, there will always be some drift errors during the tracking. If the drift errors are not taken care of by the registration step, they will accumulate to a point where tracking is no longer successful.

In general the fine registration step takes more time. Accordingly, most of the motion should be estimated by a fast tracking method and the fine registration should only be done for correction. For tracking, we use correspondence of points between the real video frames along with the depth-map information from the virtual rendering to solve a 3D-2D pose estimation problem. Since the accumulated rotation is small over a small number of consecutive real frames, linearization of the rotation matrix can be done. Thus, the 3D-2D pose estimation problem reduces to solving a linear system of equations. The same method can be used for manual registration if the manual correspondence between the real and virtual image is given. For the fine registration step, we use the approach used for tracking by Helferty et al. [6]. This can be done by replacing the optical-flow constraint equation by a similar constraint based on correlation and replacing the source image with the virtual image.

Figure 1:
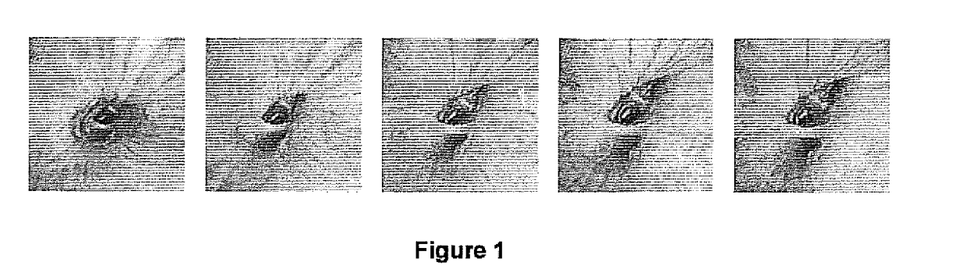
FIG. 1 shows a set of 5 consecutive bronchoscopic video (real) frames displaying motion of the bronchoscope inside the airway tree.
Figure 2:
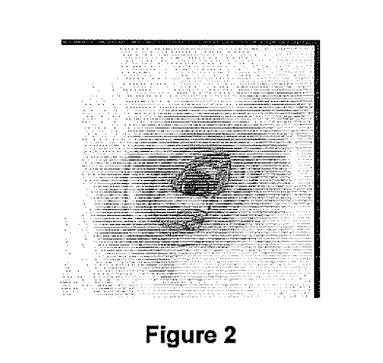
FIG. 2 shows the CT-based (virtual) endoluminal rendering of the airway surface based on the current estimate of the position and the orientation (pose) of the bronchoscope.

FIG. 1 shows a set of 5 consecutive bronchoscopic video (real) frames displaying motion of the bronchoscope inside the airway tree. The first frame is considered as the current video frame $I_{Rc}$ and the last frame is considered as $I_{R5}$. The frames in between are denoted by $I_{R2}$, $I_{R3}$ and $I_{R4}$. FIG. 2 shows the CT-based (virtual) endoluminal rendering of the airway surface based on the current estimate of the position and the orientation (pose) of the bronchoscope. The virtual image $I_v$ is visually similar to the current video frame $I_{Rc}$. The goal is to re-render the virtual image $I_v$ so that it looks like $I_{R5}$, the real frame which is five frames apart from the current video frame $I_{Rc}$. This can be done by making use of the image motion observed in the real frames, the depth-map from the virtual rendering, and the visual similarity between the virtual image and real images.

Figure 3:
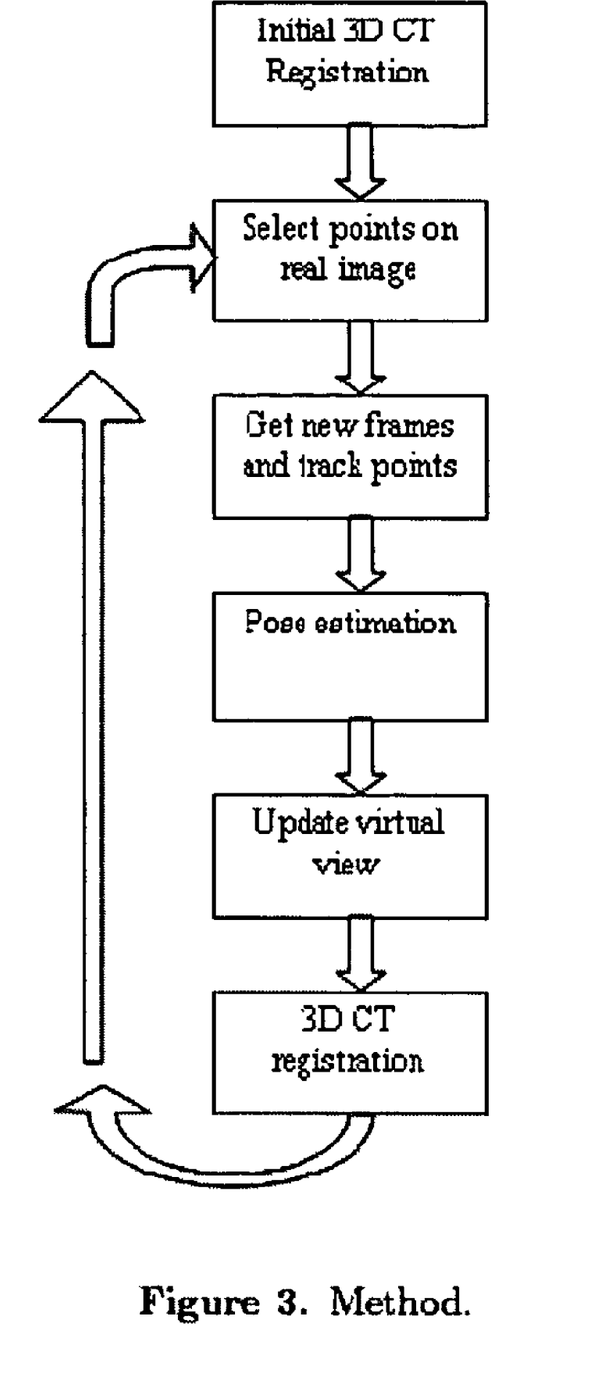
FIG. 3 shows the overall method of the invention.

FIG. 3 shows the overall method. The first step is to do an initial registration of the virtual image $I_v$ with the current real image $I_{Rc}$, either manually or automatically. The manual registration is done by giving corresponding points across the real and virtual image. In the preferred embodiment 6 points are used. Since the points in the virtual image also have the depth data associated with them denoted by $W_i$ or $(X_i, Y_i, Z_i)$, the 3D-2D pose estimation method is applied to get the current pose or the 3D motion of the bronchoscope (R,T), which will make virtual image $I_V$ look the same as the current real image $I_{Rc}$. $I_V$ is re-rendered using the pose estimate. Automatic registration is done by the fine registration step.

The second step is to choose a multiplicity of points from the current real frame $I_{Rc}$ to be tracked over a plurality of consecutive frames. In the preferred embodiment 20 points are tracked across 5 frames. Since $I_V$ is registered with $I_{Rc}$, we know the depths $W_i$ associated with each point from the current depth-map. The third step is to track these 20 points using pairwise correspondence over the next 5 frames to get their new 2D locations $(u_i, v_i)$. The fourth step is to estimate the new pose (R,T) using the 2D motion of tracked points and their initial depths $W_i$. In the fifth step, the virtual image $I_V$ is re-rendered using the new pose (R,T). The sixth step is to do fine registration between $I_V$ and $I_{R5}$ to take care of the drift errors due to tracking and then re-render $I_V$. Finally, $I_{R5}$ is assigned as the new current real frame $I_{Rc}$ and the algorithm goes from the second to the sixth step in a loop for continuous guidance.

Selection and Tracking of Feature Points

For fast coarse tracking of the bronchoscope, 20 feature points pi are selected on image $I_{Rc}$. $I_V$ is the matching virtual image for $I_{Rc}$ and hence provides the depth-map information for each $p_i$. Every $p_i$ has an associated depth given by the depth-map and its 3D location is given by $W_i$ or $(X_i, Y_i, Z_i)$. Each feature point pi is tracked over frames $I_{R2}$, $I_{R3}$, $I_{R4}$, and $I_{R5}$ to get their new image location $(u_i, v_i)$ in $I_{R5}$. The selection criterion for a feature point is entirely dependent on the method used for tracking it. It is for this reason that we explain the tracking method before the selection method.

Tracking

Once a point is selected in image $I_{Rc}$, it has to be tracked over frames $I_{R2}$, $I_{R3}$, $I_{R4}$, and $I_{R5}$. Tracking of feature points is done frame by frame by finding a matching corresponding point in the next frame $I_{Ri+1}$ for each feature point in the previous frame $I_{Ri}$. Matching is done by finding the local shift $(u_x^*, v_y^*)$, applied to previous location of point (x,y) in $I_{Ri}$, which minimizes the sum of squared differences (SSD) of image intensity patch around the point (x,y) in $I_{Ri}$ and the shifted point in $I_{Ri+1}$:

$$(u_x^*, v_y^*) = \arg\min_{(u_x, v_y)} \sum_{(p,q)} w(p,q)[I_{Ri+1}(x+u_x+p, y+v_y+q) - I_{Ri}(x+p, y+q)]^2 \quad (1)$$

In (1), w is a Gaussian window function applied to get better centering or localization of a matched point, $(u_x, v_y)$ is varied over a search window S and (p,q) is varied over a patch P. The match of point (x,y) in $I_{Ri}$ is given by $(x+u_x^*:y+v_y^*)$ in $I_{Ri+1}$.

Since the camera motion is assumed to be small between the frames, a simple translational image motion model is used, as justified by Shi and Tomasi [8]. To accommodate larger motion, a Gaussian pyramid is constructed.

The larger motion is estimated at a coarser level. This reduces the computation, since a smaller window P can be used for a template intensity patch and the search space S remains small at all the levels in the pyramid.

Selection

Before tracking, feature points $p_i$ are chosen from frame $I_{Rc}$. A feature-based approach tries to use a small amount of image data to save computation and in some cases improve robustness. For a feature-based tracking, the first step is to select a set of feature points. A point is considered better for selection if it can promise to give a good match in the next frame. According to Triggs, each image-matching method defines a corresponding self-matching-based feature point detector and if a point cannot be accurately matched with itself then it cannot be matched robustly with any other point [9]. Hence the sharpness of a correlation or SSD peak obtained by matching a shifted image patch with itself under small motion has been the key criterion for many methods [8-10].

The SSD of an image patch with itself as a function $E(u_x, v_y)$ of a shift $(u_x, v_y)$ is given by:

$$E(u_x, v_y) = \sum_{(x,y)} [I(x+u_x, y+v_y) - I(x,y)]^2 \quad (2)$$

where (x,y) is varied over a patch P. For a small shift $(u_x, v_y)$, $$E(u_x, v_y) = \sum_{(x,y)} [u_x I_x(x,y) + v_y I_y(x,y)]^2 = [u_x \ v_y] \begin{bmatrix} \Sigma I_x^2 & \Sigma I_x I_y \\ \Sigma I_x I_y & \Sigma I_y^2 \end{bmatrix} \begin{bmatrix} u_x \\ v_y \end{bmatrix} \quad (3)$$

and $$A = \begin{bmatrix} \Sigma I_x^2 & \Sigma I_x I_y \\ \Sigma I_x I_y & \Sigma I_y^2 \end{bmatrix} \quad (4)$$

is known as the autocorrelation matrix. This form of the autocorrelation matrix is valid only for a simple translational motion model. For other motion models—e.g., affine motion, the number of parameters and number of dimensions are large. The eigenvalues of the autocorrelation matrix have been used to analyze the local image structure and classify a feature as a corner or an edge [8, 10].

Zuliani et al. have analyzed the relationship between different detectors based on the eigenvalues of the autocorrelation matrix [11]. They give a criterion for feature-selection called the condition number. The condition number $K_{trans}$ measures the sensitivity of $E(u_x, v_y)$ to the perturbations $(\Delta u_x, \Delta v_y)$. It is given by:

$$K_{trans} = ||(A + \epsilon 1)^{-1}|| \quad (5)$$

where $\epsilon$ is a small number used for numerical stability. High value of a condition number means high sensitivity of the autocorrelation to the perturbations, which in turn means that the autocorrelation has a sharp peak at the point of interest.

For implementation, around 60 points are short-listed as feature-point candidates based on the strength of the image gradient at that point. If depth $Z_i$ changes much around the point $p_i$ in the virtual image $I_V$, the point may be close to a 3D edge and therefore, is not good for tracking or subsequently for pose estimation. Hence, thresholding is applied on the standard deviation of depths around the selected points to reject few more. These points are then sorted according to their condition number. Finally, the top 20 points are selected for tracking.

Pose Estimation

After a feature point $P_i$ has been selected and tracked, its 3D location $W_i$ in frame $I_{Rc}$ and its new 2D location $(u_i, v_i)$ in frame $I_{R5}$ are known. Between frames $I_{Rc}$ and $I_{R5}$, the bronchoscope has undergone a 3D motion (R,T).

Given the 3D locations $W_i$ of n points in one reference frame and their 2D images $(u_i, v_i)$, through perspective projection in another reference frame, solving for the rotation and translation (R,T) between the reference frames is known as 3D-2D pose estimation problem. Thus, the goal of the pose estimation step is to estimate (R,T) given $W_i$ and $(u_i, v_i)$.

Many different classes of algorithms have been developed to solve this problem. Closed-form solutions exist for three or four points unless they are in a critical configuration [12-14]. These methods make use of the rigid geometrical constraints between the points to solve for a polynomial system of equations. For more than 4 points, one class of methods express a system of higher-order equations as a system of linear equations (over-dimensioning) to solve for depths first and then use the solution to absolute orientation problem to solve for the pose [15, 16]. Lu et al. give a fast iterative algorithm to determine the pose [17]. However, the method introduces large bias errors in the estimate of the translation when the object is very close to the camera or the depth of the object is comparable to the distance between the object and the camera, which holds true in our domain of application.

Since the feature tracking is done over a few frames at a time, it can be assumed that the accumulated rotation is small. Our method uses this assumption to linearize the rotation matrix. Our method is very close to Lowe's method [18] and the least-squares adjustment step done by Haralick et al. [19].

A 3D rotation matrix R is given by $$R = R_x R_y R_z \quad (6)$$

where $$R_x = \begin{bmatrix} 1 & 0 & 0 \\ 0 & \cos\theta & -\sin\theta \\ 0 & \sin\theta & \cos\theta \end{bmatrix} \quad (7)$$

$$R_y = \begin{bmatrix} \cos\psi & 0 & \sin\psi \\ 0 & 1 & 0 \\ -\sin\psi & 0 & \cos\psi \end{bmatrix} \quad (8)$$

$$R_z = \begin{bmatrix} \cos\phi & -\sin\phi & 0 \\ \sin\phi & \cos\phi & 0 \\ 0 & 0 & 1 \end{bmatrix} \quad (9)$$

where $\theta$, $\psi$ and $\phi$ are the rotation angles around each axis. For small values of $\theta$, $\psi$ and $\phi$, the rotation matrix can be written as $$R = I + [\omega]_x = I + \begin{bmatrix} 0 & -\phi & \psi \\ \phi & 0 & -\theta \\ -\psi & \theta & 0 \end{bmatrix} \quad (10)$$

A 3D world point W transformed by (R, T) is given by:

$$W' = R * W + T = (I + [\omega]_x) * W + \quad (11)$$

-continued $$T = \begin{bmatrix} X \\ Y \\ Z \end{bmatrix} + \begin{bmatrix} \theta \\ \psi \\ \phi \end{bmatrix} \times \begin{bmatrix} X \\ Y \\ Z \end{bmatrix} + \begin{bmatrix} t_x \\ t_y \\ t_z \end{bmatrix} = \begin{bmatrix} X + \psi Z - \phi Y + t_x \\ Y + \phi X - \theta Z + t_y \\ Z + \theta Y - \psi X + t_z \end{bmatrix}$$

The image of W' through perspective projection is given by:

$$u = f\frac{X'}{Z'} \quad (12)$$
$$v = f\frac{Y'}{Z'}$$

where f is the focal length. Henceforth, without loss of generality, f will be assumed to be 1.

Given n world points $(X_i, Y_i, Z_i)$ and their image points $(u_i, v_i)$ in another reference frame, we have to find $$(R^*, T^*) = \arg\min_{(R,T)} \sum_{i=1}^{n}\left[\left(u_i - \frac{X'_i}{Z'_i}\right)^2 + \left(v_i - \frac{Y'_i}{Z'_i}\right)^2\right] \quad (13)$$

where $(X'_i, Y'_i, Z'_i)$ are given by (11). We can solve for (R, T) using following equations:

$$u_i = \frac{X_i + \psi Z_i - \phi Y_i + t_x}{Z_i + \theta Y_i - \psi X_i + t_z} \quad (14)$$
$$v_i = \frac{Y_i + \phi X_i - \theta Z_i + t_y}{Z_i + \theta Y_i - \psi X_i + t_z}$$
$$i = 1 \ldots n$$

This gives an over-constrained system of linear equations:

$$\begin{bmatrix} \vdots & \vdots & \vdots & \vdots & \vdots & \vdots \\ -u_iY_i & u_iX_i + Z_i & -Y_i & 1 & 0 & -u_i \\ v_iY_i - Z_i & v_iX_i & X_i & 0 & 1 & -v_i \\ \vdots & \vdots & \vdots & \vdots & \vdots & \vdots \end{bmatrix} \begin{bmatrix} \theta \\ \psi \\ \phi \\ t_x \\ t_y \\ t_z \end{bmatrix} = \begin{bmatrix} \vdots \\ u_iZ_i - X_i \\ v_iZ_i - Y_i \\ \vdots \end{bmatrix} \quad (15)$$

The linear system of equations (15), can be solved using singular value decomposition (SVD), although care should be taken to make very small singular values equal to zero while solving. Since the linearized form (10) of R is an approximation, we have to a iterate few more times to reach the correct solution for (R,T). Using the current solution for (R,T), the 3D points $W_i$ are transformed to get a new estimate for $W'_i$. The residual transformation (R',T') should be determined by treating $W'_i$ as the new $W_i$ in (11). Then, (R,T) are updated as follows:

$$R = R'^*R \quad T = R'^*T + T \quad (16)$$

The method typically converges in 3 or 4 iterations.

3D CT Registration

After the pose estimation step, the virtual image $I_V$ is re-rendered using the estimate for (R,T). This brings $I_V$ visually closer to $I_{R5}$. But due to the presence of drift errors, $I_V$ is still not a good match for $I_{R5}$. Using correlation as a criterion for visual match and the depth-map associated with $I_V$, the fine registration step estimates the residual motion (R',T') between $I_V$ and $I_{R5}$. $I_V$ is re-rendered using (R',T') to complete one loop of the guidance algorithm.

Registration Using Correspondence

A fast way to register the two sources together is to use the same method as used for tracking. The only difference being that the correspondence will be found between the virtual image $I_V$ and real image $I_{R5}$. The points, however, are selected on $I_{R5}$ using the autocorrelation criterion. Since most of the information is contained in dark areas, the points are selected so that they sample all the dark regions. The selected points are matched with $I_V$ using the correlation as the matching criterion in a Gaussian pyramid set up. The next step is to run the pose estimation algorithm and update $I_V$ using the estimated pose. Although this method is fast, the matching does not work well for all image pairs $I_V$ and $I_{R5}$. The accuracy of the method depends on the distance of the bronchoscope from the branching point in the airway and the number of branches seen in $I_{R5}$. Manual registration uses this same method, but the corresponding points are provided manually.

Registration Using Maximization of Correlation

Helferty et al. use the optical flow constraint equation along with the linearization of rotation matrix and the depth-map from the virtual image to do tracking [6]. We propose to use the same approach for fine registration of the virtual image $I_V$ with the real image $I_{R5}$.

In the method given by Helferty et al., the goal is to register a real source image with a real target image by iteratively warping the source image towards the target image [6]. The 2D image motion of a point in the source image or optical flow $(u_{xi}, v_{yi})$ is governed by the 3D rotation and translation through:

$$u_{x_i} = \frac{\psi Z_i - \phi Y_i + t_x}{\theta Y_i - \psi X_i + t_z} \quad (17)$$
$$v_{y_i} = \frac{\phi X_i - \theta Z_i + t_y}{\theta Y_i - \psi X_i + t_z}$$

Its derivation is almost same as given above. The optical flow constraint equation used to determine $(u_x, v_y)$ is given by:

$$u_x I_x + v_y I_y + I_d = 0 \quad (18)$$

Using (17) and (18), a system of linear equations is set up to iteratively solve for (R, T). After each step, warping and computation of the gradients of the source image is done for the next iteration until convergence. The details can be found in [6].

In our case, the source image is $I_V$ and the target image is $I_{R5}$. The optical flow constraint (18) is based on the SSD criterion for matching. Since in our case, both the virtual image $I_V$ and the real image $I_{R5}$ are from two different sources, the optical flow constraint cannot be used directly. However, if $I_V$ and $I_{R5}$ are normalized by subtracting the mean before registration, then (18) becomes a valid constraint and then both (17) and (18) can be used together for fine registration.

EXAMPLES

Figure 4A:
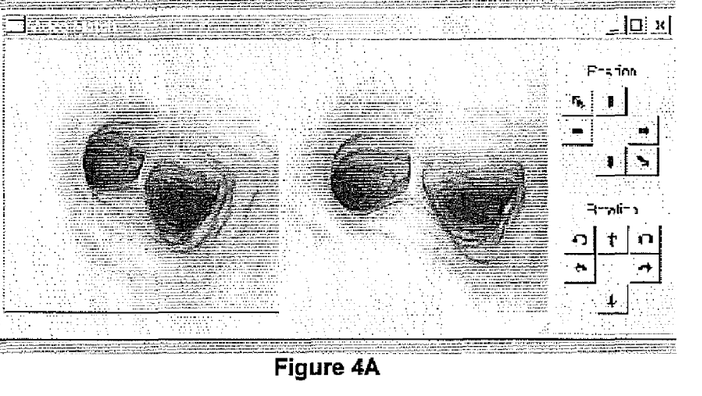
FIG. 4A shows the initial unregistered pair of virtual images.
Figure 4B:
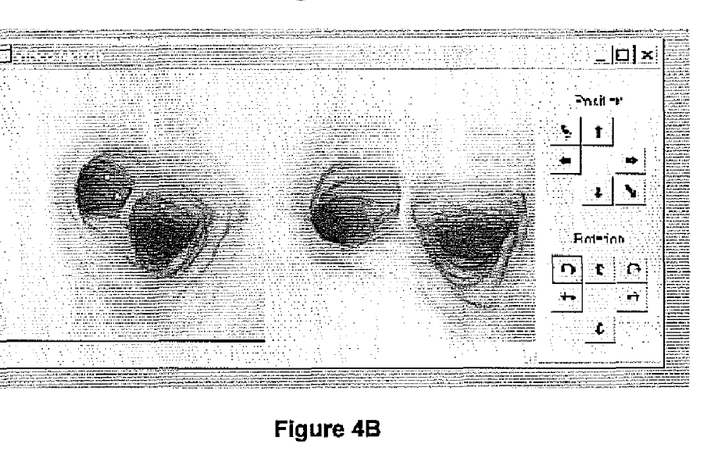
FIG. 4B shows the 6-point correspondence given manually.
Figure 4C:
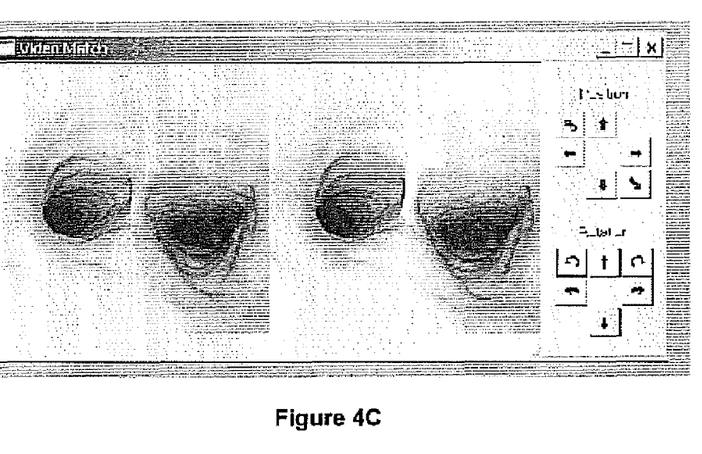
FIG. 4C shows the registered pair after the pose estimation step.

FIGS. 4A-4C demonstrate the manual registration step applied to a pair of virtual images. The six corresponding points are given manually across the two images. The unknown pose is computed by the pose estimation method using the correspondence and the depth-map associated with the virtual image on left. The virtual image on left is re-rendered using the estimate for pose. This results in a match between the left and the right image. The pose estimation method is very fast and generates the match instantaneously. The accuracy of the registration is dependent on the quality of the correspondence.

Figure 5:
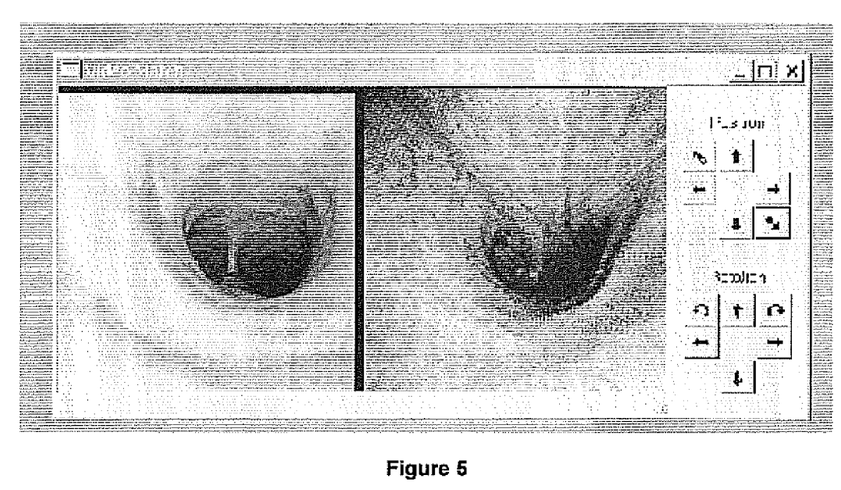
FIG. 5 illustrates the use of the manual registration step for the initial registration of the virtual and real image to start the guidance method.
Figure 6A:
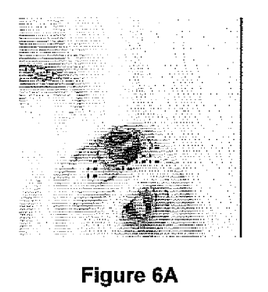
FIG. 6A shows the virtual image $I_v$ close to the real image $I_{Rc}$ on right with the matching points.
Figure 6B:
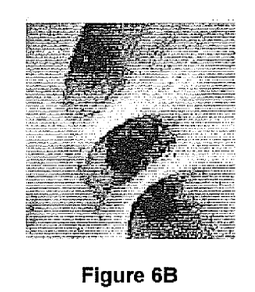
FIG. 6B shows the real image $I_{Rc}$ close to the virtual image $I_v$ on left with the latching points.
Figure 6C:
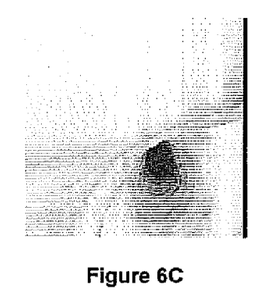
FIG. 6C shows the re-rendered virtual image $I_v$ after the pose estimation step.

FIG. 5 illustrates the use of the manual registration step for the initial registration of the virtual and real image to start the guidance method. FIGS. 6A-6C show the result of using the method for pose estimation by Lu et al. and demonstrates its unsuitability for our domain [17]. Although the correspondence has small errors (on the order of one pixel), we get large errors in the computed translation. Given below is a comparison between the correct pose (R,T) and computed pose (R1, T1):

$$R = \begin{bmatrix} 1 & -0.0061 & 0.0061 \\ 0.0064 & 0.9991 & -0.0417 \\ -0.0058 & 0.0417 & 0.9991 \end{bmatrix}$$

$$T = \begin{bmatrix} 0.0412 \\ -0.1444 \\ -0.1171 \end{bmatrix}$$

$$R1 = \begin{bmatrix} 0.8154 & 0.5763 & 0.0542 \\ 0.5781 & -0.8155 & -0.0262 \\ -0.0291 & -0.0527 & 0.9982 \end{bmatrix}$$

$$T1 = \begin{bmatrix} 2.2667 \\ -0.1280 \\ 16.0598 \end{bmatrix}$$

The link to the Matlab code for the pose estimation method by Lu et al. is given in the paper [17].

Figure 7A:
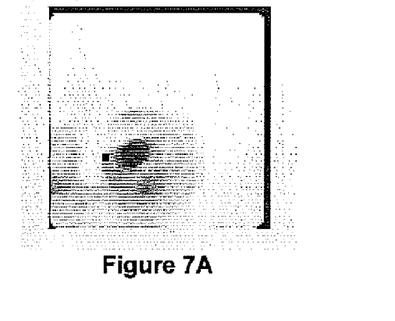
FIGS. 7A-7B show the computed corresponding matching point on the real image $I_{R5}$, given an input point on the virtual image $I_v$.
Figure 7B:
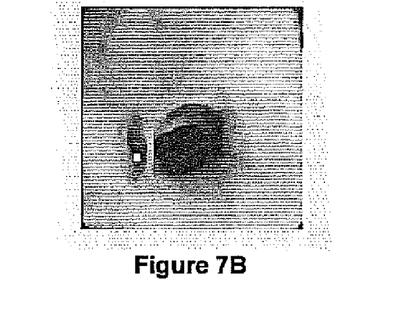

After feature selection, tracking and pose estimation, the fine registration step is required to take care of the drift errors. The fine registration step can either be based on correspondence or on optical-flow. FIGS. 7A and 7B show the computed corresponding matching point on the real image $I_{R5}$, given an input point on the virtual image $I_v$. On the real image, the white point shows the initial guess for the match. The black point shows the final match obtained using the correlation criterion in a Gaussian pyramid set up. The use of Gaussian pyramid takes care of a large motion and saves on computation time by reducing the search space S.

Figure 8A:
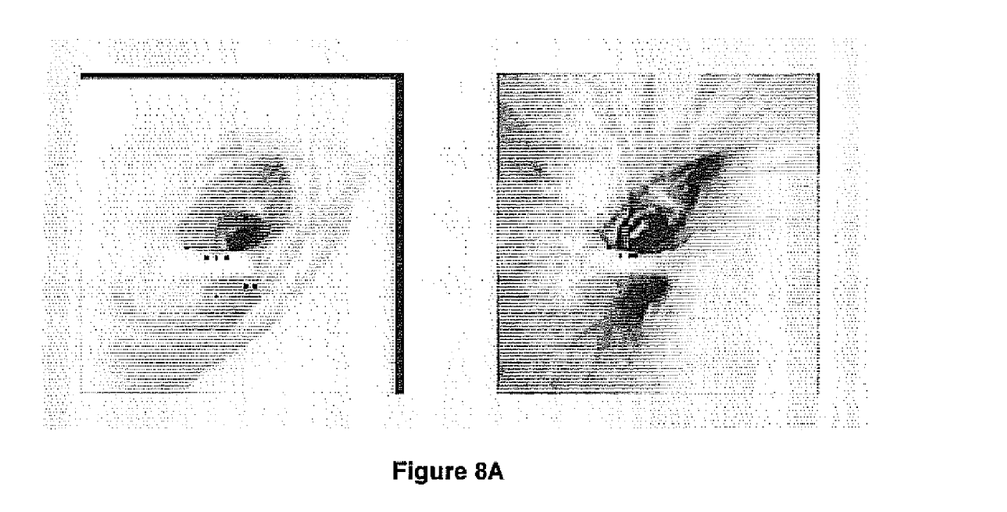
FIGS. 8A and 8B show the results obtained by applying a registration step to a virtual image and a real image.
Figure 8B:
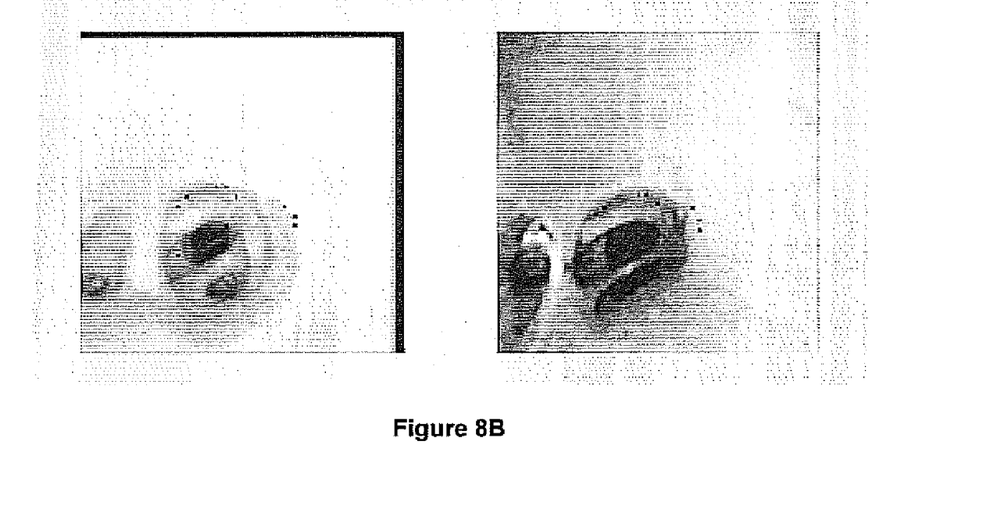

FIGS. 8A and 8B show the results obtained by applying the registration step to a virtual image and a real image. The points used for correspondence are displayed, too. Although for these two cases, the registration result is good, in general this is not the case. The accuracy of the registration step depends on the quality of the correspondence. Good correspondence is not found, when the bronchoscope is either near or far from the bifurcations. In that case, the optical-flow-based fine registration step is used.

Figure 9A:
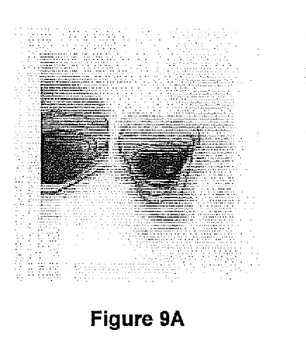
FIGS. 9A-9C illustrate the optical-flow-based method for registration by Helferty et al.
Figure 9B:
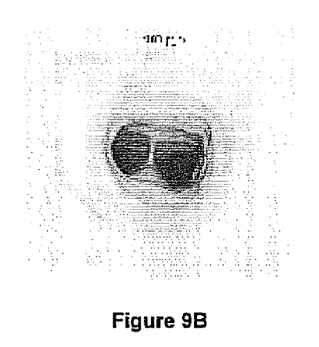
Figure 9C:
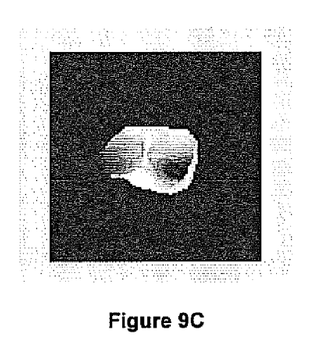

FIGS. 9A and 9B illustrate the optical-flow-based method for registration by Helferty et al. [6]. The source image is warped towards the target image, iteratively to recover the residual motion. It is a gradient-based approach which can quickly recover the residual motion between $I_v$ and $I_{R5}$. FIGS. 10a-c illustrate the fine registration step for a virtual and video image pair, with an example warped virtual image after motion estimation.

Fast tracking is an essential step in keeping the two sources together for guidance during bronchoscopy. It is not possible to escape from drift errors due to tracking, as they arise partially from small errors in the 3D image data. A fine registration step is then necessary to take care of drift errors. Feature-based 3D-2D pose estimation is a fast and stable technique to do tracking. It does not suffer from instability associated with computing an essential matrix. If correspondence is computed across both the real and virtual images, then this same set up can be used for registration as well.

At least two other alternatives are available for guidance in the case of bronchoscopy. These alternatives include:

1. The previously acquired image data is a prerecorded bronchoscopic video image sequence with associated depth information and the live source is incoming video from a bronchoscope.
2. The previously acquired image data is a prerecorded bronchoscopic video image sequence with associated depth information and the live source is a stream of incoming virtual images, as may be acquired when interactively navigating through a 3D CT image.

The application has far-reaching applications, particularly in the field of image-guided endoscopy.

In summary, we disclose a new 3D-2D pose estimation method based on linearization of the rotation matrix. The method is iterative and has fast convergence in case of small rotation. Using normalized images in the optical-flow constraint equation makes it possible to use the gradient-based registration method by Helferty et al. for fine registration [6]. This approach is faster than using simplex method or Powell's method for registration.

REFERENCES

1. I. Bricault, G. Ferretti, and P. Cinquin, "Registration of real and CT-derived virtual bronchoscopic images to assist transbronchial biopsy," IEEE Transactions On Medical Imaging, Vol. 17, No. 5, pp. 703-714, Oct 1998.
2. W. E. Higgins, J. P. Helferty, and D. R. Padfi, "Integrated bronchoscopic video tracking and 3D CT registration for virtual bronchoscopy," SPIE Medical Imaging 2003: Physiology and Function: Methods, Systems, and Applications, A. Clough and A. Amini (eds) 5031, pp. 80-89, May 2003.
3. K. Mori, D. Deguchi, J. Hasegawa, Y. Suenaga, J. Toriwaki, H. Takabatake, and H. Natori, "A method for tracking the camera motion of real endoscope by epipolar geometry analysis and virtual endoscopy system," MICCAI '01: Proceedings of the 4th International Conference on Medical Image Computing and Computer-Assisted Intervention, pp. 1-8, 2001.
4. H. Shoji, K. Mori, J. Sugiyama, Y. Suenaga, J. Toriwaki, H. Takabatake, and H. Natori, "Camera motion tracking of real endoscope by using virtual endoscopy system and texture information," SPIE Medical Imaging 2001: Physiology and Function from Multidimensional Images, Chin-Tu Chen and Anne V. Clough (eds) 4321, pp. 122-133, May 2001.

5. K. Mori, T. Enjoji, D. Deguchi, T. Kitasaka, Y. Suenaga, J. Toriwaki, H. Takabatake, and H. Natori, "New image similarity measures for bronchoscope tracking based on image registration between virtual and real bronchoscopic images," SPIE Medical Imaging 2004: Physiology and Function from Multidimensional Images, Amir A. Amini and Armando Manduca (eds) 5369, pp. 165-176, April 2004.

6. J. P. Helferty and W. E. Higgins, "Combined endoscopic video tracking and virtual 3D CT registration for surgical guidance," IEEE Int. Conference on Image Processing, pp. 11-961-11-964, Sept 2002.

7. R. I. Hartley and A. Zisserman, Multiple View Geometry in Computer Vision, Cambridge University Press, ISBN: 0521623049, 2000.

8. J. Shi and C. Tomasi, "Good features to track," IEEE Conf. Computer Vision and Pattern Recognition, pp. 593-600, June 1994.

9. B. Triggs, "Detecting keypoints with stable position, orientation and scale under illumination changes," European Conference on Computer Vision, pp. IV 100-113, May 2004.

10. C. Harris and M. Stephens, "A combined corner and edge detector," Alvey Vision Conference, pp. 147-151, 1988.

11. M. Zuliani, C. Kenney, and B. S. Manjunath, "A mathematical comparison of point detectors," IEEE Image and Video Registration Workshop, June 2004.

12. M. Fischler and R. C. Bolles, "Random sample consensus: A paradigm for model fitting with applications to image analysis and automated cartography," Comm. ACM 24(6), pp. 381-395, 1981.

13. R. Horaud, B. Canio, and O. Leboullenx, "An analytic solution for the perspective 4-point problem," Computer Vision, Graphics, and Image Processing (1), pp. 33-44, 1989.

14. R. M. Haralick, C. Lee, K. Ottenberg, and M. Nolle, "Analysis and solutions of the three point perspective pose estimation problem," Computer Vision and Pattern Recognition, pp. 592-598, 1991.

15. A. Ansar and K. Daniildis, "Linear pose estimation from points or lines," IEEE Transactions on Pattern Analysis and Machine Intelligence 25, pp. 578-589, May 2003.

16. L. Quan and Z. Lan, "Linear n-point camera pose determination," IEEE Transactions on Pattern Analysis and Machine Intelligence 21(8), pp. 774-780, 1999.

17. C. Lu, G. D. Hager, and E. Mjolsness, "Fast and globally convergent pose estimation from video images," IEEE Transactions on Pattern Analysis and Machine Intelligence 22(6), pp. 610-622, 2000.

18. D. G. Lowe, "Fitting parametrized three-dimensional models to images," IEEE Transactions on Pattern Analysis and Machine Intelligence 13(5), pp. 441-450, 1991.

19. R. M. Haralick, H. Joo, C. Lee, X. Zhuang, V. G. Vaidya, and M. B. Kim, "Analysis and solutions of the three point perspective pose estimation problem," IEEE Transactions on Systems, Man, and Cybernetics 19(6), pp. 1426-1446, 1989.

We claim:

1. A method of providing guidance in real-time or near real-time in conjunction with an endoscopic procedure, comprising the steps of:
   providing previously acquired three-dimensional (3D) image data of a body lumen;
   receiving a continuous live sequence of endoscopic video image data of the body lumen during a procedure from an endoscope; and
   registering the previously acquired 3D image data of the body lumen and the live endoscopic video image data of the body lumen to provide guidance to a user of the endoscope wherein the step of registering includes estimating the 3D location of the endoscope using the live sequence of endoscopic video image data and the previously acquired 3D image data.

2. The method of claim 1, wherein the step of registering the previously acquired 3D image data and the live video image data is used to guide said endoscope during the procedure.

3. The method of claim 1, wherein the previously acquired 3D image data is derived from virtual image data.

4. The method of claim 1, wherein the previously acquired 3D image data is derived from computerized tomographic (CT) image data.

5. The method of claim 1, wherein the previously acquired 3D image data is derived from a prerecorded video source.

6. The method of claim 1, wherein the registration step includes the steps of:
   a) estimating a three-dimensional location of the endoscope using (i) known motion information from said received video image data, and (ii) local depth information obtained from the previously acquired 3D image data; and
   b) determining a new pose of the endoscope based on the 3D location estimated in step (a).

7. The method of claim 1, wherein said registration step is performed after a sequence of consecutive video image frames is received.

8. The method of claim 2, wherein the endoscope is a bronchoscope.

9. The method of claim 8, further comprising the step of advancing the bronchoscope from a bifurcation in an airway tree.

10. The method of claim 6, wherein the step of determining a new pose is based on linearization of a rotation matrix.

11. The method of claim 6, further including the step of performing a fine registration step to minimize errors associated with estimating the 3D motion of the endoscope.

12. The method of claim 6, wherein the registration step further includes the steps of:
   (c) updating the previously acquired 3D image data in accordance with the new pose; and
   (d) repeating steps (a) through (c) until the guidance is terminated.

13. The method of claim 6, wherein the previously acquired 3D image data are derived from a magnetic resonance image (MRI) image data or computerized tomographic (CT) slices.

14. The method of claim 6, further comprising the step of rendering a virtual image frame of the body lumen corresponding to the new pose of the endoscope.

15. The method of claim 11, wherein the fine registration step is based upon a gradient-based Gauss-Newton method.

16. A method of providing guidance in conjunction with an endoscopic procedure, comprising the steps of:
   providing previously acquired three-dimensional (3D) image data of a body lumen;
   acquiring a continuous live sequence of endoscopic video image data of the body lumen during the procedure from an endoscope; and
   registering and tracking the previously acquired 3D image data and the live endoseopic video image data in real time or near real-time to obtain a current pose of the endoscope; and wherein the step of registering and tracking is performed by:
  a) estimating the 3D location of the endoscope using the steps of:
     registering the previously acquired 3D image data and live video image data to obtain a current depth map;
     choosing a plurality of points associated with the live video image data;
     tracking the points over a plurality of consecutive frames to estimate the two-dimensional (2D) motion of the tracked points; and
     using the 2D motion of the tracked points and the current depth map to derive the three-dimensional (3D) motion of the instrument;
  b) determining a new pose based on the estimating step;
  c) updating the current pose based upon the new pose; and
  d) repeating steps a) through c) to complete guidance.

17. The method of claim 16, wherein:
3D locations of the plurality of points and corresponding 2D images are determined using perspective projection.

18. The method of claim 16, wherein the estimating step is based on a linearization of a rotation matrix.

19. A system for guiding an endoscope through a body lumen, comprising:
  a database storing previously acquired 3D image data of a body lumen;
  an input for receiving a continuous live sequence of endoscopic video image data of the body lumen; and
  a processor in communication with the database and the input, the processor being configured to perform the following functions:
  estimate the 3D location of the actual physical location of the endoscope based on the live endoscopic video image data and the previously acquired 3D image data, and
  register the previously acquired 3D image data and the live endoscopic video image data in real time or near real-time, thereby providing guidance to a user of the endoscope.

20. The system of claim 19, wherein the database storing previously acquired 3D image data of the body lumen includes depth information.

21. The system of claim 19, wherein the processor is further configured to perform a fine registration step to minimize errors associated with estimating three-dimensional (3D) motion.

22. The system of claim 19, wherein the previously acquired 3D image data are derived from one of a magnetic resonance image (MRI) image data and computerized tomographic (CT) slices.

23. The system of claim 19, wherein the endoscope input is a bronchoscope input to obtain the live video image data.

24. The system of claim 20, wherein the estimate function is further configured to:
  a) estimate three-dimensional (3D) location using the depth information and tracking of a plurality of points associated with the live video image data; and
  b) perform a pose estimation to determine a new pose of the endoscope.

25. The system of claim 24, wherein the processor is further configured to linearize a rotation matrix to perform the pose estimation.

26. The method of claim 24, wherein said plurality of points is 20 points.

27. The system of claim 21, wherein the fine registration uses a gradient-based Gauss-Newton method.

28. The system of claim 21, wherein the fine registration includes:
  computing a virtual image of a body lumen;
  applying a correlation-based cost to register the virtual image and the live video image data.

29. The method of claim 7, wherein said sequence of video image frames is 5 consecutive video frames.

* * * * *